United States Patent [19]

Bowman

[11] 4,283,448
[45] Aug. 11, 1981

[54] COMPOSITE POLYTETRAFLUOROETHYLENE ARTICLE AND A PROCESS FOR MAKING THE SAME

[75] Inventor: Jeffery B. Bowman, Flagstaff, Ariz.

[73] Assignee: W. L. Gore & Associates, Inc., Newark, Del.

[21] Appl. No.: 121,365

[22] Filed: Feb. 14, 1980

[51] Int. Cl.³ .................. B29C 27/02; B29D 23/00
[52] U.S. Cl. ................................ 428/36; 138/103; 138/DIG. 3; 156/86; 156/187; 156/304.6; 239/145; 239/547; 264/230; 264/248; 428/421
[58] Field of Search .............. 264/248, DIG. 71, 230, 264/262, 263, 313, 267, 269, 127; 156/304, 86, 187, 244, 27, 304.6; 428/421, 422, 35, 36; 138/DIG. 3, 103; 239/145, 547; 210/500 R

[56] References Cited

U.S. PATENT DOCUMENTS

| | | | |
|---|---|---|---|
| 612,897 | 10/1898 | Ellis | 144/309 J |
| 3,207,644 | 9/1965 | Hobson et al. | 428/421 |
| 3,767,500 | 10/1973 | Tally et al. | 428/421 |
| 3,953,566 | 4/1976 | Gore | 264/127 |
| 4,061,517 | 12/1977 | Dutton et al. | 156/304 |

*Primary Examiner*—W. E. Hoag
*Attorney, Agent, or Firm*—John S. Campbell

[57] ABSTRACT

A porous polytetrafluoroethylene (PTFE) article which is made up of a number of smaller articles with a microstructure of nodes interconnected by fibrils, these articles having been joined to one another such that their microstructure is virtually unaltered across the join. A process for producing such a PTFE article by closely abutting small-shaped PTFE segments and applying a force perpendicular to the seam while heating to a temperature above the crystalline melt point of the segments.

4 Claims, 6 Drawing Figures

COMPOSITE POLYTETRAFLUOROETHYLENE ARTICLE AND A PROCESS FOR MAKING THE SAME

FIELD OF THE INVENTION

This invention relates to a process for making a novel composite article of expanded polytetrafluoroethylene.

BACKGROUND OF THE INVENTION

Polytetrafluoroethylene (hereinafter "PTFE") has excellent heat resistance, chemical resistance, insulation resistance, non-adhesiveness and self-lubrication. This polymer has found wide use in medical, industrial and recreational fields.

A recent invention (U.S. Pat. No. 3,953,566) provides a process for manufacturing highly porous, yet high strength, shaped, PTFE articles. This process involves blending highly crystalline, fine powder PTFE with a liquid lubricant, extruding this mixture through a die which may have desired cross-sectional configuration, and subsequently expanding the shaped article in one or more directions at rates in excess of 10% per second.

Products produced by this process have found widespread acceptance in the industrial, medical, electrical, and clothing arts. The process is somewhat limited in that it is not readily adaptable to the production of large articles with complex cross-sections. A need for such articles is found, for example, in the industrial filtration arts and in large vessel vascular surgery. Although large composite articles can be manufactured by joining smaller articles together by such conventional methods as sewing, welding or gluing, such articles have a discontinuity at the seam. While in many applications this does not present any severe problems, in others such as filtration and body part replacement, it is extremely important that the structure be as uniform as possible over the entire article. If welding or gluing is used to produce large articles, a dense non-porous area is produced. On the other hand, sewing may produce areas which have a greater porosity than the rest of the article. It has been found that the microstructure of nodes and fibrils present in products produced by U.S. Pat. No. 3,953,566 is particularly desirable as both a filter media and as surface for contacting blood and other body fluids. It would, therefore, be desirable to produce composite, complex shapes by joining articles of expanded PTFE with this microstructure in such a manner that the microstructure remains virtually uninterrupted across the join or seam.

BRIEF DESCRIPTION OF THE INVENTION

An objective of the present invention is a process for producing a composite, shaped, PTFE article. Such an article is produced by joining segments of smaller-shaped articles. These smaller segments are held close together and their temperature raised to a temperature above the crystalline melt point of the segments. They are then allowed to cool to room temperature to facilitate handling of the article. A further objective of this invention is the production of a composite, shaped, PTFE article by the above process, with a virtually uninterrupted microstructure of nodes interconnected by fibrils across the join.

DETAILED DESCRIPTION OF THE INVENTION

Bonding of PTFE to PTFE by mechanically holding the two parts in contact and heating them above the crystalline melt point of PTFE is known in the art. Generally, however, this has resulted in a solid non-porous seam. The present invention utilizes a modification of the process to produce a product in which the node-fibril microstructure present in both parts is maintained virtually uninterrupted across the seam. The result is that a seam-free product is produced. In the present context, the term "edges" is used to refer to that portion of the expanded PTFE article which is to be bonded together and "seam" refers to the area so bonded. Articles refer to any shaped cross-section, e.g., tube, rod, sheet or segment.

PTFE material is available in a variety of shapes, including sheets, rods and tubes from W. L. Gore & Associates, Inc. The articles to be bonded are cut to the required size. Care must be taken to ensure that the edges to be joined are clean, that is neither ragged or dirty. The two edges are then placed in close proximity, i.e., touching one another.

If expanded PTFE is heated above its crystalline melt point while unrestrained, the material will tend to shrink and coalesce into a solid mass. In order, therefore, to ensure that the two articles to be bonded together remain in contact while being heated, mechanical means must be employed to so hold them.

Figure 1:
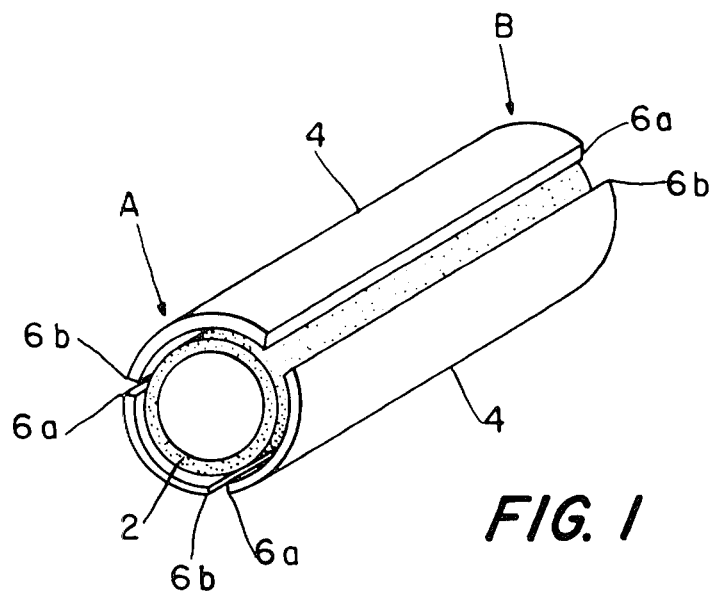
FIG. 1 is a schematic illustration of one of the embodiments of the present invention.

For example, as illustrated in FIG. 1, a large tube can be made from sheets or sections from a number of smaller tubes. The sheets 4 are trimmed at their edges 6(a) and 6(b) to ensure that these edges are clean, that is, not ragged or dirty. The sheets 4 are then laid around a mandrel 2. The edges 6(a) and 6(b) of each sheet 4 are closely butted to the edges 6(a) and 6(b) of the adjoining sheet. The ends of the sheets, A and B, are fixed at these points to the mandrel. This can be achieved in a variety of ways, such as hose clamps or tying the sheets to the mandrel by wire. The reason for so fixing the tube, is to prevent longitudinal retraction of the PTFE on heating.

A strip of expanded PTFE film about 0.75 inches wide and having a longitudinal Matrix Tensile Strength of about 70,000 p.s.i. is spirally wound around the sheets on the mandrel and fastened at the end of the mandrel so it cannot unwrap. Upon heating, this restraining film shrinks, applying pressure on the sheets and keeping the edges 6(a) and 6(b) in close contact. A satisfactory film is commercially available as GORE-TEX expanded filament from W. L. Gore & Associates, Inc., P.O. Box 1220, Elkton, Md. 29121. Although wrapping with an expanded PTFE film is a preferred means of mechanically restraining and holding the edges of the sheets in contact during heating, other means may be used.

The important factor is that there must be some force perpendicular to the seam during sintering. When the film wrapped around the tube retracts, it supplies the necessary force.

The heating of the wrapped tube can be achieved in a salt bath, an air oven, a radiant oven or other heating means. A suitable salt bath can be a molten mixture of sodium nitrites and nitrates and is maintained at a temperature above the crystalline melt point of the segments. The tube is then removed and allowed to cool while still being held restrained. The time above the crystalline melt point will vary depending on the mass of material involved and resin properties. The exact time to produce an optimum bond will depend on a number of factors such as mass of material and the configuration of the shape being produced. Such a time, however, is easily determined with a minimum of experimentation. The following example is intended to illustrate and not limit the present invention. The technique can be used in any of a variety of shapes and sizes where it is important to maintain a virtually uninterrupted microstructure across any joining line or seam.

EXAMPLE I

Three 6.5 cm long, 120° segments were cut from 20 mm inside diameter tubes which had been produced according to the teachings of U.S. Pat. No. 3,953,566. The resin used was Fluon 123 which is a fine powder, PTFE resin commercially available from ICI America. These segments were carefully trimmed to ensure that the edges to be butted were clean. The segments were then carefully laid around a smooth, 20 mm O.D., stainless steel tube. The segments were arranged so that they butted closely together. They were then spirally wrapped with a 0.75 inch wide expanded PTFE film having a Matrix Tensile Strength of about 70,000 p.s.i. which was manufactured according to U.S. Pat. No. 3,962,153.

The mandrel was then placed in an air oven at 380° C. for 12 minutes. Upon removal from the air oven, the mandrel was allowed to cool to room temperature and the formed PTFE tube was carefully slid off the mandrel. For the purpose of this experiment, the wrapping film was carefully removed from the tube in order to photomicrograph the structure at the seam.

Figure 2:
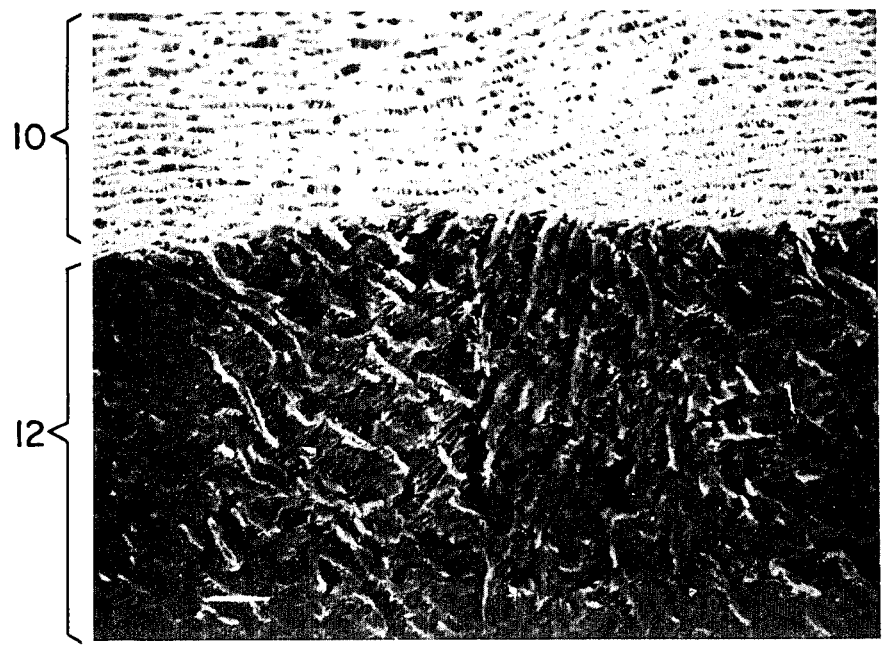
FIGS. 2-4(b) are electromicroscopic photographs of various surfaces of a tube produced in accordance with the invention.

FIG. 2 is an angled electromicroscopic photograph of one of the seams made in Example I. The top portion 10, is a topographical view of the inside surface of the tube. The bottom portion 12, is a cross-section view of the tube. In FIG. 2, the seam runs from X to Y. The magnification is 146 times.

Figure 3A:
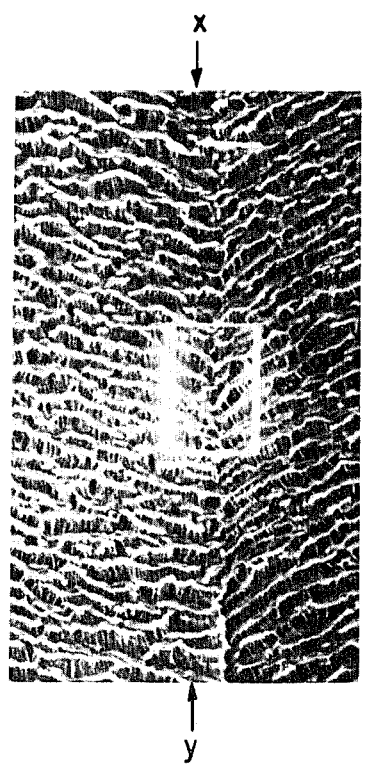
Figure 3B:

FIG. 3(a) is an electromicroscopic photograph of the inside surface of the tube made in Example I. The seam runs from X to Y. The magnification is 122 times. FIG. 3(b) is an electromicroscopic photograph of the inserted area in FIG. 3(a). The seam runs from X to Y and the magnification is 610 times.

Figure 4A:
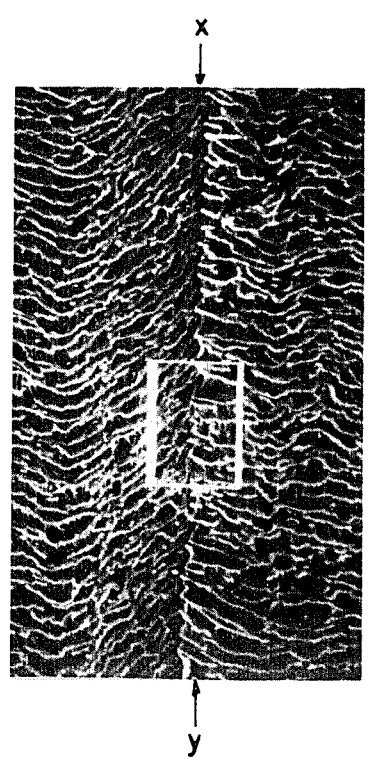
Figure 4B:

FIG. 4(a) is an electromicroscopic photograph of the outside surface, after removal of the film, of the tube made in Example I. The seam runs from X to Y and the magnification is 90 times. FIG. 4(b) is an electromicroscopic photograph of the inserted area shown in FIG. 4(a). The seam runs from X to Y and the magnification is 450 times.

From these electromicroscopic photographs, it is surprising to observe that the node-fibril microstructure is virtually uninterrupted across the seam. Although a small scale example was used to illustrate this invention, this technique can be readily extended to cover large tubes up to several inches in diameter. Equally, the technique can be used with any of a variety of shapes and is not limited to tubular cross-sections. For example, sheets of uniaxially expanded PTFE with thicknesses ranging from about 0.005" to more than 0.100" could be joined together in the following manner. Restrain the PTFE sheets in the direction of their expansion, butt them in place between 1/16" thick sheets of 60 durometer silicon rubber (two sheets of rubber on each side of the PTFE that are not quite butted together with a gap of about 0.010" between them which corresponds to the seam in the PTFE sheets), and place the PTFE and rubber sheets in a press with platens heated to about 380° C. The press could be closed to apply a very small pressure to the sheets sitting on the rubber. This would supply the necessary perpendicular force to the seam, this time in a planar configuration. After an appropriate time, approximately 15 minutes, the electrical heaters on the press could be turned off and the platens cooled by a stream of compressed air. When the platens had cooled to room temperature, the pressure could be released and the sheets removed.

I claim:

1. A process for joining a plurality of shrinkable expanded porous polytetrafluoroethylene segments, each having a microstructure of nodes interconnected by fibrils, such that the microstructure is virtually uninterrupted at the seam joining said segments, comprising the steps of:
   (a) arranging said segments such that their edges are disposed in abutting relationship;
   (b) causing a pressure to be applied perpindicular to said abutting edges;
   (c) causing said segments to be restrained from shrinking in any direction;
   (d) heating said segments while they are so held, to a temperature above the crystalline melt point of polytetrafluoroethylene for a predetermined time; and
   (e) allowing said segments to cool while still being held restrained and under pressure.

2. A composite article made in accordance with claim 1.

3. A method for manufacturing a porous composite tube from a plurality of segments of shrinkable expanded porous polytetrafluoroethylene, each having a microstructure of nodes interconnected by fibrils such that the microstructure is virtually uninterrupted at the seam joining said segments comprising the steps of:
   (a) forming a tube of expanded porous polytetrafluoroethylene segments by disposing said segments around a suitable mandrel in abutting relationship;
   (b) winding a film of high strength shrinkable expanded porous polytetrafluoroethylene with a microstructure of nodes interconnected by fibrils around said segments;
   (c) restraining said segments from shrinking longitudinally;
   (d) bonding and shrinking said film to said segment, thereby applying pressure perpindicular to the edge of said segments by heating to a temperature above the crystalline melt point of polytetrafluoroethylene for a predetermined time; and
   (e) allowing said wrapped bonded segments to cool.

4. A composite article made in accordance with claim 3.

* * * * *